United States Patent [19]
Py

[11] Patent Number: 5,746,728
[45] Date of Patent: May 5, 1998

[54] FLUID PUMP WITHOUT DEAD VOLUME

[76] Inventor: Daniel Py, 40, rue Franklin, 78100 St.Germain En Laye, France

[21] Appl. No.: 534,609

[22] Filed: Sep. 27, 1995

[30] Foreign Application Priority Data

Oct. 3, 1994 [FR] France ................... 94 11785

[51] Int. Cl.⁶ .......................... A61M 35/00; B65B 37/00
[52] U.S. Cl. .......................... 604/298; 604/294; 222/207; 222/378
[58] Field of Search .................... 604/294–302; 222/378, 207, 209, 211

[56] References Cited

U.S. PATENT DOCUMENTS

| | | | |
|---|---|---|---|
| 4,220,264 | 9/1980 | Gamadia | 222/207 |
| 4,623,337 | 11/1986 | Maurice | 604/298 |
| 5,085,651 | 2/1992 | Py | 604/298 |
| 5,207,659 | 5/1993 | Pennaneac'h | 604/298 |
| 5,238,156 | 8/1993 | Andris | 222/209 |
| 5,320,845 | 6/1994 | Py | 424/427 |
| 5,351,862 | 10/1994 | Weag | 222/209 |
| 5,462,208 | 10/1995 | Stahley et al. | 222/209 |

FOREIGN PATENT DOCUMENTS

WO 93/10852  6/1993  WIPO.

*Primary Examiner*—John G. Weiss
*Assistant Examiner*—David J. Cho

[57] ABSTRACT

A pump for delivering a fluid contained in an elastic phial includes a pump body and a movable piston fitted inside the pump body. The front end of the pump body is located on a fluid-outlet side, and the front end includes an outlet orifice (11) sealed off by an elastic membrane (24). The outlet orifice is connected to a pump duct (18) inside the pump body, and the pump duct 18 is in turn connected to a fluid-inlet orifice (15). An end (2) of the movable piston is hermetically fitted within the pump duct (18) with slight friction, and the displacement of the end (2) of the piston relative to the portion of the pump body between the inlet orifice (15) and the a stop position (16) near the outlet orifice (11) determines the quantity of fluid expelled from the pump body. The inlet orifice allows a predetermined quantity of fluid to be trapped at the end of the pump duct (18) before being expelled through the outlet orifice (11). With the exception of the front end of the pump body, the pump body and the movable piston are totally enveloped by the elastic phial.

14 Claims, 6 Drawing Sheets

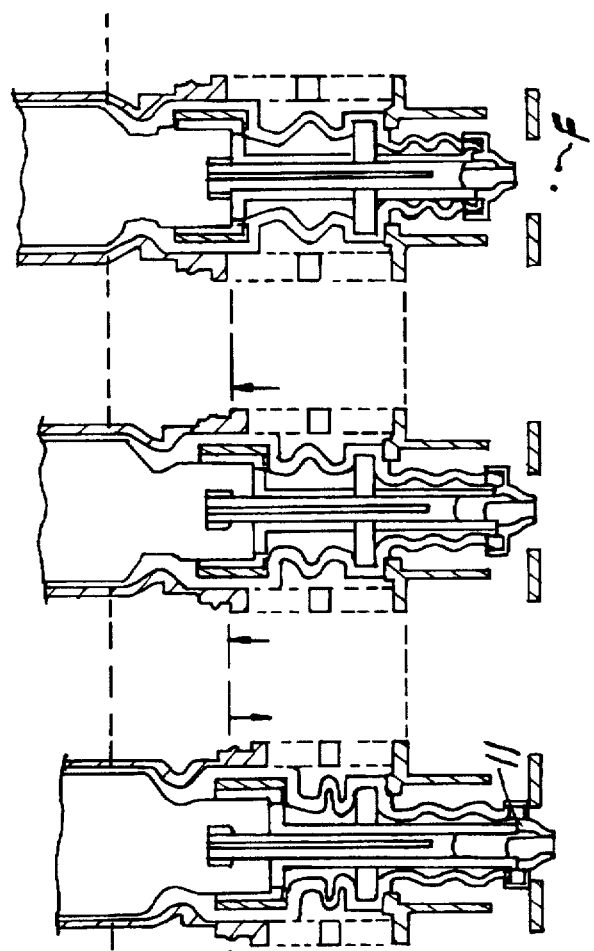
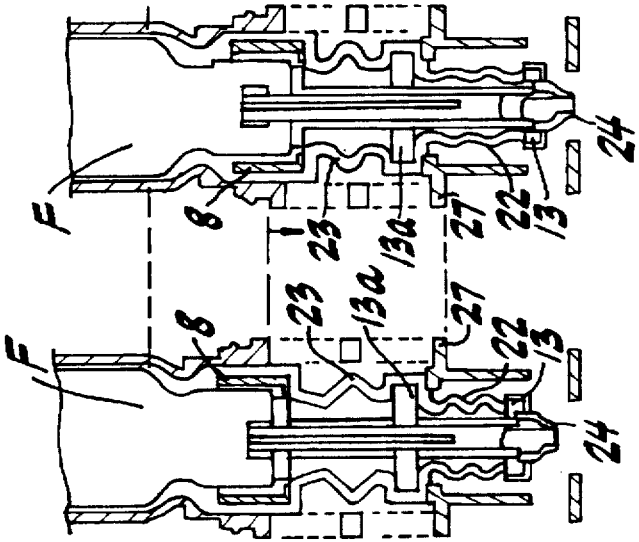

FLUID PUMP WITHOUT DEAD VOLUME

BACKGROUND OF THE INVENTION

The present invention concerns a pump, especially a three-piece phial-pump without dead volume for delivering a fluid, particularly without preservative and filled under sterile conditions.

In certain industries, especially the pharmaceutical industry, pumps are always sought after that enable delivery of a fluid, preferably without dead volume so as to avoid, for example, contamination of a sterile fluid, or the degradation of an unstable fluid, on contact with the oxygen in the air, into toxic or inactive products.

We should explain here that dead volume is defined as being the volume between the closing device of a pump and the open air.

Moreover it would be advantageous to have a pump that delivered in a regular manner a precise quantity of fluid and, preferably, whatever the volume concerned both small volumes in the order of 10 µl and much greater volumes.

Furthermore, preferably the quantity of fluid delivered should depend neither on gravity nor the speed of activation of the pump.

It would be equally desirable to have a pump in which the absence of air or preservative in the phial with which such a pump is fitted would preserve a stable formulation and moreover prevent the pollution of this formulation, for example a liquid medium without preservative.

In addition, a phial fitted with such a pump should be able to benefit from almost zero exposure to the air whilst the phial is being filled, thus ensuring the sterility of the contents.

SUMMARY OF THE INVENTION

The manufacture of such devices is as delicate as the volume to be delivered is small, for example in the order of 10 µl. This is why the present invention has for its object a pump for the delivery of a fluid contained in an elastic phial, characterised in that it comprises:

a pump body having a front end or tip on the fluid outlet side, the said front end comprising an outlet orifice sealed off by an elastic membrane, and continuing backwards through a pump duct with a fluid inlet orifice;

a movable piston fitted inside the pump body, the relative displacement of the end of the piston in relation to the pump body between the inlet orifice and a stop position located towards the outlet orifice thus determining the quantity of fluid expelled on displacement, the end of the piston fitting hermetically by slight friction against the duct, the inlet orifice being of a sufficient size for only the preset quantity of fluid to be trapped in the end of the pump duct for its expulsion through the outlet orifice, the pump body and the piston being totally enveloped by the phial, with the exception of the front end of the pump body. The fluid can, for example be a paste, but preferably a gel and more particularly a liquid.

The front end of the pump body, tip or "nose", comprises an outlet orifice preferably in the form of a, for example, cylindrical channel, opening into a pump duct, the latter being for example conventionally in the form of a cylindrical tube, the outlet orifice or channel and pump duct preferably lying in the same general direction. The outer orifice is preferably a channel advantageously positioned essentially axially along the length of the pump. However, as is clear to an expert within the field, the channel may be of any shape, in particular an elbow shape, so as to ensure for example a projection perpendicular to the axis of the pump.

The elastic membrane may be made of any well-known state-of-the-art elastic material, for example rubber, an elastomer, and preferably thermo-elastic materials such as those available from the AES Company under the name of VISKAFLEX, from the DUPONT Company under the name of ALCRYN or HYTREL, from the DSM Company under the name SARLINK, or from the SHELL Company under the name KRATON. The elastic membrane has, at the outlet orifice, a sufficient thickness to form a one-way valve towards the outlet. In other words by working the piston towards the outlet orifice, the force exerted on the piston enables the said valve to open thus enabling the fluid to be expelled. By contrast, after expelling the liquid, if the piston is then drawn back the valve becomes hermetically sealed and, in the pump duct, a reduced pressure or vacuum is created.

The pump duct has a fluid inlet orifice enabling the fluid to fill through the latter. This inlet orifice may be of any shape, rounded, elongated, and may be in the shape of a channel, a slit, a groove, etc.

As a syringe, the pump according to the present invention comprises a movable piston fitted inside the pump body; the piston is preferably fitted along the length of the device. "Movable", means that the piston is movable in relation to the body in which it is housed, without necessarily specifying which, the piston or body, moves. This piston can move between a stop position located towards the fluid outlet orifice, and a position beyond the fluid inlet orifice. The stop may be preferably, as in a conventional syringe, the end of the pump duct on the outlet side, however, another stop may be made, if desired, before this end.

In the first case, after the fluid is expelled by the relative working of the piston and pump body, the volume of fluid held between the outlet valve and the piston end will be reduced merely to the volume of the evacuation channel. In the second case, in addition to the evacuation channel, the fluid will occupy a certain volume of the pump duct.

As in a conventional syringe, the end of the piston of the pump according to the present invention fits hermetically by slight friction against the pump cylinder.

It will thus be understood that when the piston is drawn in the opposite direction to the outlet orifice, a reduced pressure is created in the pump duct, the reduced pressure being "broken" when the end of the piston reaches the level of the fluid inlet orifice. At this point the fluid is sucked into the pump duct which it fills.

During the relative displacement of the piston towards the outlet orifice, when the piston goes beyond the inlet orifice, it thus traps in the pump duct a certain volume of fluid. The set volume between this position and the most extreme, stop position of the movable piston corresponds to the preset quantity of fluid which will be expelled by the pump.

The compression of the fluid by the piston, the compression being achieved, for example and preferably with the aid of an elastic means or by pressure with the aid of the thumb on the piston, enables the elastic membrane forming a valve to open and the fluid to be expelled.

It will be understood that the fluid inlet orifice must be of a sufficient size since, if it were too small, on moving the piston, a certain quantity of fluid could be expelled through the outlet without having the time to return to the rest of the contents of the phial.

This is why, when a very precise dosage of the quantity of fluid expelled is required, the inlet orifice is preferably of a sufficient size for only the set quantity of fluid to be trapped in the end of the pump duct in order for it to be expelled through the outlet orifice.

As can be seen from the above, the rest position of the pump according to the invention is the position where the piston is at the stop. This is why preferably the pump according to the invention has an elastic means of returning the piston to the stop position. These elastic means are well known to the expert within the field and are such as a spring, the spring being fitted inside or outside the pump, along the piston's axis of displacement; the said spring may be made of a metal or plastic material, the nature of the spring being adapted to the fluid contained in the bottle when the said spring is fitted inside the phial in contact with the fluid.

These elastic means may comprise especially the envelope of the elastic phial itself as illustrated below in the Figures. It may for example comprise a concertina, or annular convex part of sufficient thickness to form a means of return. The envelope is for example at this level integral on one side with the pump body and on the other with the piston by means of rings with which these elements may be fitted. These rings can co-operate with corresponding slots which in this case are made in the envelope. In order to strengthen the means of return it is possible for example to use, if desired, two return elements such as concertinas located more particularly on either side of the retaining ring, integral with the piston as illustrated below.

The elastic membrane may be a separate piece of the elastic phial. However, in preferred conditions of embodiment of the pump described above, the elastic membrane and the elastic phial form a single piece. The number of pieces of the pump according to the invention may therefore be remarkably reduced. Indeed, according to the invention, it is possible to have an elastic phial fitted with a pump comprising just three pieces: initially a phial made of an elastic material constituting at the same time the fluid receptacle, the membrane forming the one-way valve and the elastic means of returning from the relative pump body/piston position to the rest position; the other two pieces are the pump body and the piston.

In other preferred conditions, the elastic phial according to the present invention has at least one part such as a thickening, adapted to filling the phial with the aid of a hollow needle, of such a type that after piercing, filling and withdrawing the hollow needle, the piercing is hermetically sealed.

Preferably, the specially-designed part is a thickening of the wall of the elastic phial. This thickening may be at a precise point, as illustrated below, annular or general.

It is clear for an expert within the field that a precise thickening is preferred, especially so as to economise on the amount of raw material used to manufacture the envelope; if the ease of filling is to be enhanced by avoiding having to position the pump for this purpose, an annular thicknening would be preferable.

A preferred pump according to the invention comprises a pump body with a frontal ring, fitted close to the fluid outlet. Such a frontal ring enables the elastic phial to be hermetically fixed to the pump body. Such a ring also enables the embodiment of elastic means for returning the piston to the stop position.

The pump body also preferably comprises a rear ring, which can perform several functions. On the one hand, in the case of a device for manual use, this rear ring can, for example, serve as a grip for the user's fingers. This rear ring can also, in the case of using a return spring, serve for mounting the latter. Lastly in the case where the pump according to the invention is a device comprising just three pieces, this rear ring can co-operate with the envelope of the elastic phial, at the rear of a concertina constituting the elastic means of return.

The piston of a pump according to the present invention also preferably has a ring enabling, in the case of manual use, the piston to be gripped for example by the user's fingers. This ring may also co-operate with the phial envelope so as to constitute the concertina means of return of the piston.

As above the ring may engage in the slots in the phial according to the invention.

If the above elements may have any suitable shape, a circular shape, similar to that of a conventional glass or plastic syringe, is particularly preferred.

The ring of the above piston is preferably an incomplete ring.

Such a conformation enables the piston to be fitted into the pump body as will be explained in further detail in the Figures.

Under preferred conditions, the above piston has the general conformation of an elongated element, corresponding to a conventional piston, the elongated element having a plurality, preferably three, of elements in the shape of a ship's anchor, each thus comprising a radial element, at the end of which is an arc-shaped element. The plurality of arcs then forms the incomplete ring referred to above. In such a case, for example, the pump body comprises a cylindrical element, comprising at its front end a ring and at its rear end another cylindrical ring, of larger diameter than the diameter of the arcs described above, the front base of the rear cylindrical ring being cut away so that the above anchors can pass through the base of the cylinder thus enabling, by means of slots corresponding to the above radial elements, and made in the cylinder comprising the pump body, the longitudinal displacement of the piston.

The slots made in the pump body perform two functions: on the one hand they enable the displacement of the piston, by the radial elements sliding along the axis of the slots, and on the other the end of the slots on the front side constitutes the fluid inlet orifice enabling the fluid to reach the final pump duct corresponding to the preset volume of fluid to be expelled.

The dynamics of a pump according to the present invention are as follows:

Let us assume that the equilibrium position is the position in which the piston is at the stop. As is clear for the man skilled in the art, the displacements referred to in the present application are in general relative displacements. Indeed preferably, the piston may be kept stationary and the pump body moved as illustrated below, or the pump body kept stationary and the piston moved to achieve the outlet of the fluid.

When the piston draws back, it creates a cavity whose state of pressure is a partial vacuum, indeed the outlet orifice is blocked off by the elastic membrane, preventing the entry of air into the pump. On drawing back further, the piston ends up by reaching the level of a fluid inlet orifice. At this point the pump duct quickly fills with fluid. The piston can then be pushed back or left to move on to the stop position. When the piston again reaches the level of the fluid inlet orifice, on reaching the end of the latter, it traps a preset volume of fluid. The volume between this extreme position and the stop position of the piston, then determines the quantity of fluid expelled. From this moment ejection of the fluid occurs.

A pump according to the invention has many advantages which it also confers to an elastic phial fitted with such a pump. The preset volume proposed for the pump may be adjusted by altering both the cross-sectional area of the cavity or pump duct and the length of this cavity by changing the depth of the inlet orifice. The dose is constant and depends neither on gravity nor the activation speed of the pump. It can only depend on the spring effect given to the relative pump body/piston movement, and this for a given viscosity and orifice diameter.

The wall of the phial can perform the role of both a receptacle and return spring thus reducing a pump/phial according to the invention to a minimum of pieces, and the minimum number can be just three pieces for the entire assembly.

The pump according to the invention is very simple to assemble especially when it comprises just a piston in a body, all fitted inside an elastic envelope.

The pump ensures the projection of drops; for this reason it does not require special positioning of the receiving surface or surface that projects the drops. In the case for example of use for ophthalmic purposes, such a pump dispenses with the need for the patient to tilt his head backwards: he can just as readily tilt it forwards or remain in an upright position.

The fact that the drops are projected also makes enables this pump to be used in weightless conditions.

The use of an elastic wall for the envelope makes it possible to achieve in one piece the following functions in particular:

- a one-way valve function, enabling operation without drawing in air or the actual substance being delivered; the pump also makes it possible to dispense formulations without preservative which may be used repeatedly without the risk of contamination of the inside of the phial.
- a phial function; the elasticity of the wall in fact enables the wall to cave in gradually as the liquid is evacuated by the pump. The elastic wall allows a fluid to be injected through itself, particularly through sites designed for this purpose: either two thickened membranes to be perforated with the aid of a hollow needle, or an injection device actually inserted in the mould when the elastic envelope is being manufactured so that the injection of this elastic substance in the mould ensures a perfect seal between the injection device and the wall itself. Injection and filling can be achieved by means of needles or trocars. It can also be achieved either by dilation of a specially-designed expandable ring, or by applying an increase in pressure on the wall at the level of an injection device inserted by moulding for this purpose.

Injection may be followed by simply withdrawing the needle, trocar or any other means of injection, thanks to the elasticity of this wall and its return to a sealed position. The seal can be further improved for example by heat-sealing or sealing by any other means: ultrasound, radio, phased radiation, etc., which ensures a perfect seal at the point where the injection was made.

The injection or filling of such a pump may be associated with a suction which precedes and/or accompanies and/or follows filling so as to eliminate any residual gas in the phial after filling.

The dose delivered on each activation of the pump does not vary, whatever the ambient pressure, because no gas exists inside the system, the system having moreover no dead space.

The device according to the present invention also allows sealed filling in the receptacle thus formed, without air, without gas, and whatever the ambient pressure, and without the seal undergoing succesive possible variations in ambient pressure. This filling can be achieved under sterile conditions without the fluid, liquid or gel, coming into any contact with the surrounding environment; it can therefore be achieved in particular totally protected from the air or filling gas until final use. Such filling may be achieved by the injection of fluids with the aid of a hollow needle through the aforesaid thickenings. Preferably the procedure is then performed under a controlled atmosphere on the microbiological plan, for example by using laminar flow.

Moreover, since the flexible parts are elastic parts, such a device ensures a minimum of particles.

Lastly, as can be seen, such a pump makes it possible to dispense with a propellent, especially a fluoridated propellent or any other gas whose variations in temperature would cause the doses to vary and whose presence would require an additional wall to prevent the propellent from mixing with the active constituents.

The pump according to the invention has remarkable applications, particularly in ohpthalmology. It may in particular be fitted with a housing such as the one described in U.S. Pat. No. 5,267,989, introduced here as a reference, and also allows a device to be created that enables a fluid to be projected into the conjunctival sac of the eye without essentially causing any sensation of pain or discomfort, due to the very precise reserve of energy which can be conferred to the drops being propelled.

This is why the present invention also has as its object a pump for projecting a consistently reproducible volume of fluid into the conjunctival sac of the eye without essentially causing any sensation of pain or discomfort, comprising a reservoir made of elastic material, a pump body, a piston which can move inside the pump body and an elastic means for returning the piston to the stop position, the elastic means of return being calibrated so as to avoid a sensation of pain or discomfort on projecting the fluid.

BRIEF DESCRIPTION OF THE DRAWINGS

FIG. 6 shows a sequence of cross-sectional views of the phial pump, the sequence illustrating the operation of the phial-pump.

DESCRIPTION OF THE PREFERRED EMBODIMENTS

Figure 1:
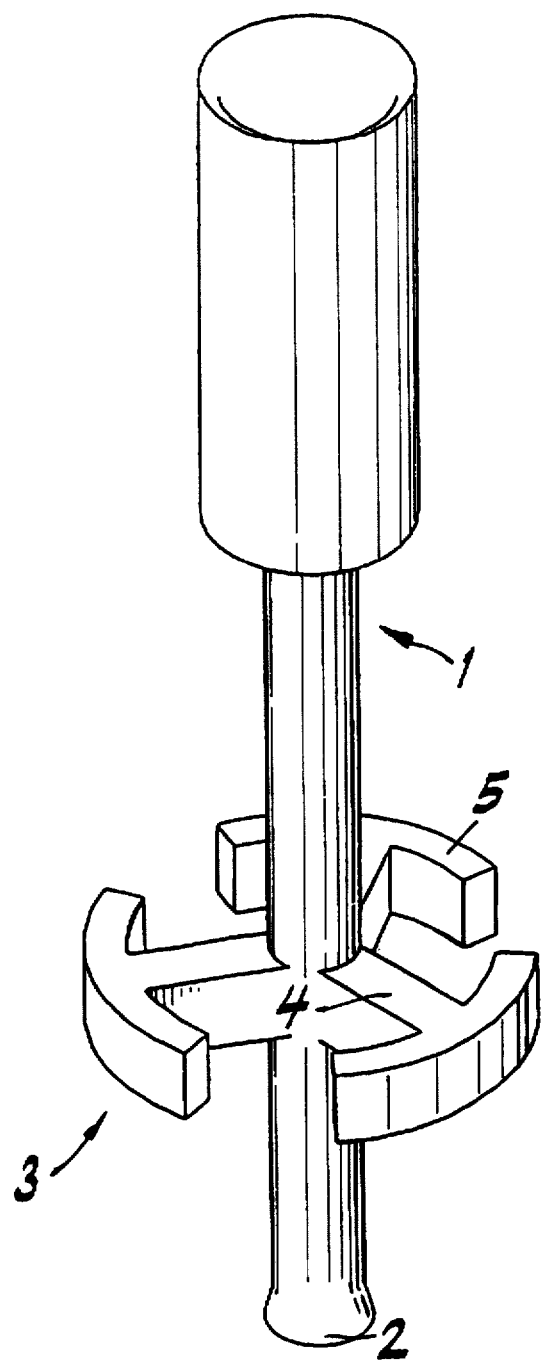
FIG. 1 is a perspective view of an embodiment of a piston to be incorporated as a part of an embodiment of the pump according to the present invention.

FIG. 1 shows a piston comprising a large longitudinal plunger 1 at the front end of which is a flange 2 designed to ensure the seal of the cavity of the pump body when the piston increases the pressure therein;

ship's-anchor-shaped fins 3, numbering three in this configuration. Each of the latter has a spoke 4 at the end of which is an arc 5; in the configuration referred to below, three spokes and, at the end of each spoke, an arc, thus making a total of three arcs.

Figure 2:
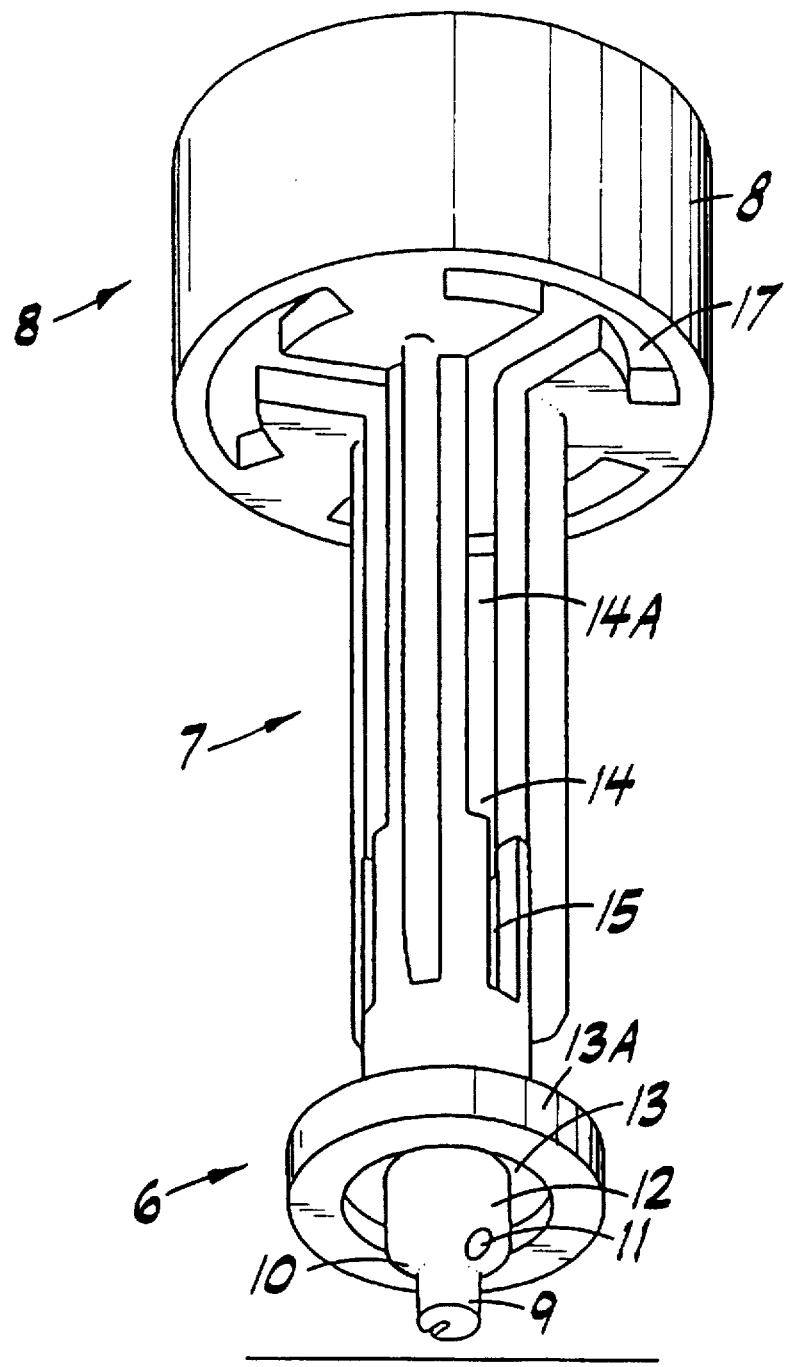
FIG. 2 is a perspective view of an embodiment of a pump body to be incorporated as a part of an embodiment of the pump according to the present invention, which pump body is intended to cooperate with the piston illustrated in FIG. 1.

FIG. 2 represents a pump body, made up of three main parts: the front part, or "nose" 6; the middle part, or "sleeve" 7; and the rear part, or "body" 8 of the pump proper.

Nose 6 may have a purely cylindrical or truncated-cone configuration; here, it comprises a small cylinder 9 at the tip followed by a truncated-cone area 10, itself perforated by the evacuation orifice 11 of the pump. Behind the truncated-cone part is another cylindrical part 12 and, behind this cylindrical part 12, an annular groove 13 serving to seal the elastic envelope which we shall refer to subsequently; this annular groove separates the nose proper from a disc or "frontal disc" 13a.

Sleeve 7 is a cylindrical sleeve inside which is the pump cavity. The cylindrical wall of sleeve 7 is perforated by longitudinal slots 14 in which slide piston spokes 4: here, three slots—one for each piston spoke.

Each slot has two portions:

a wider rear portion 14 for the piston spokes to slide along;

a narrower front portion constituting the communication orifice between the external liquid and the pump cavity and forming an inlet orifice 15. The height of this pump cavity determines the level at which the piston will effect a compression upon the fluid. It therefore determines the volume of the dose to be ejected.

On the inner wall of this sleeve, in its frontmost part following the pump nose, is stop 16 comprising an annular undercut, shown in the following FIG. 3, which houses the annular flange of the piston when the pump is in the at-rest or closed position. This undercut 16 enables the front annular flange 2 of the piston to exert a very slight compression after initial assembly, so as to keep the rest of the pump in perfect occlusion without causing the front flange of the piston to creep whilst storing the pump prior to its use. It is thus impossible for the air or liquid contained in the ejection orifice 11 of the nose, here an ejection channel, to come into contact with the liquid contained in the rest of the pump or phial.

The pump body 8 comprises a cylindrical cavity in continuity with the sleeve, and of a decidedly larger diameter, and will itself be housed in the rear ring of the envelope in order to activate the pump.

In the front part of this element there are cutaway sections 17 enabling fins 3 to pass through so as to fit the piston into the pump body.

In the case illustrated here, the pump body is movable whereas the piston will be held in a stationary position.

Figure 3:
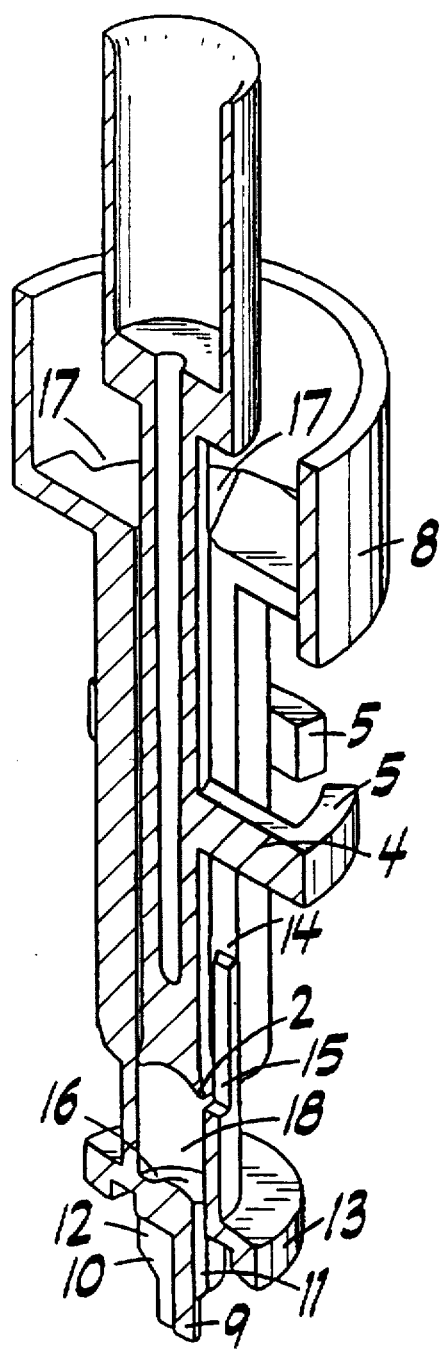
FIG. 3 is a lateral cross-sectional view of the piston shown in FIG. 1 fitted into the pump body shown in FIG. 2.

FIG. 3 represents the piston fitted inside the pump body. In addition to some of the above elements, the front stop 16 of the piston with its undercut is shown. Also shown is an inlet orifice, and the position of the piston inside the body is such that if the latter moves forwards, it will block off, in cavity 18 or pump duct, the preset volume of fluid admitted through orifice 15. Also shown is a spoke 4, installed in a longitudinal slot in which it is capable of sliding. On the rear side of the pump body, also shown is a cutaway section 17 enabling a fin to pass through. It is therefore possible to see that, compared to a conventional syringe, the pump and body have three annular parts 12, 5 and 8.

Figure 4:
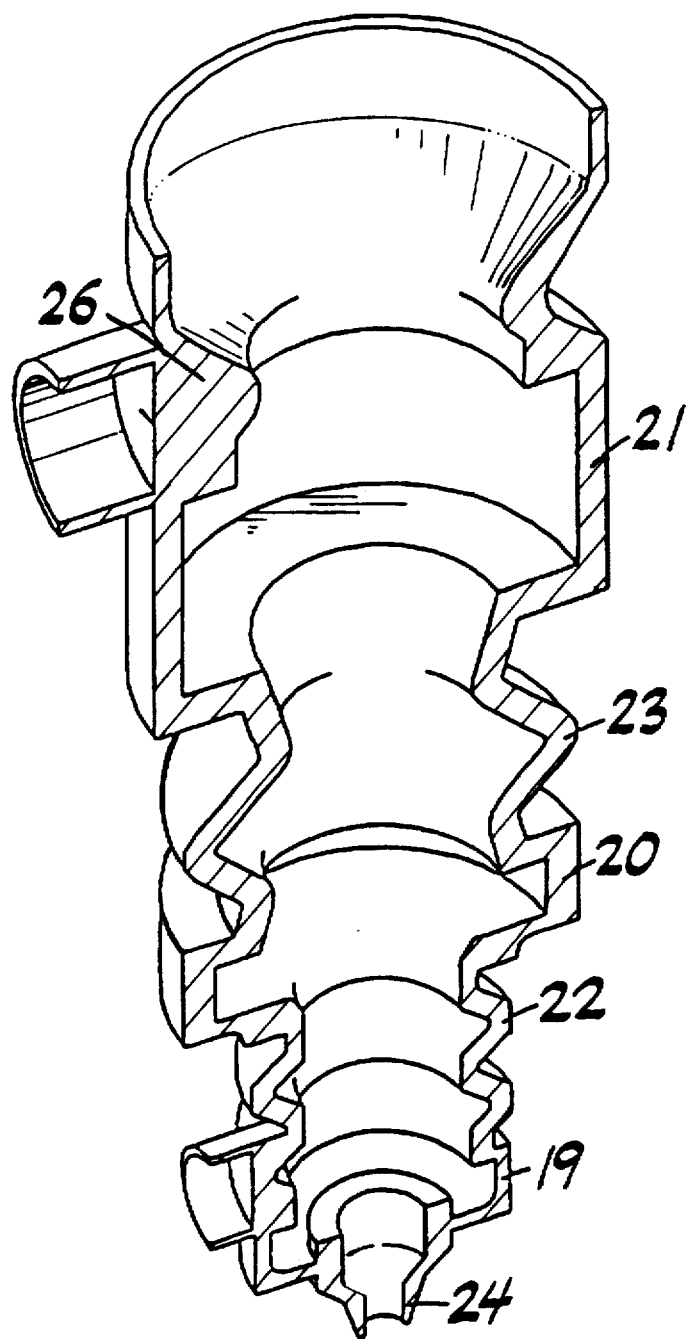
FIG. 4 is a lateral cross-sectional view of an embodiment of an envelope intended to cooperate with the piston shown in FIG. 1 and the pump body shown in FIG. 2 to form an embodiment of the phial-pump according to the present invention.

The elastic envelope is represented in FIG. 4, it comprises three rings: a front ring 19, a middle ring 20 and a rear ring 21, limiting between them a front concertina 22 and a rear concertina 23. Front ring 19 co-operates with ring 13a of the pump body, middle ring 20 co-operates with the incomplete ring formed by arcs 5 on the piston, and rear ring 21 co-operates with rear ring 8 of the pump body. The rings of the elastic envelope securely retain the rings of the other two pieces; in particular the assembly at the level of rings 13a and 19 is perfectly hermetic. Moreover, at the frontmost level of the envelope, elastic membrane 24 is shown, forming a one-way valve towards the outlet which comprises the complementary parts of small cylinder 9, of truncated-cone area 10.

It will also be seen that this envelope comprises two parts which have been specially designed to enable the passage of hollow needles with a view to filling the phial-pump with a fluid, liquid or gel, these are areas 25 and 26. The latter have indeed a greater thickness than that of the surrounding areas. Moreover, these areas each comprise a small cylinder capable for example of being heat-sealed under pressure between two heated jaws. Such a cylindrical device may be replaced for example by an extra thickness raised towards the outside of the envelope, thus protruding onto the outer wall, and onto which a heated piece may be applied so as to melt this raised part in order totally to seal the orifice having enabled the penetration of a needle.

Lastly, it will be noted that in FIG. 4, the rear part of the envelope serving solely as a receptacle has not been shown here.

Such a pump is assembled as follows: firstly the piston is fitted into the pump body until the front annular flange reaches the stop. The pump is thus in the at-rest closed position The pump is then fitted into the elastic envelope whilst jets of compressed gas dilate the elastic envelope during assembly enabling the latter with a minimum of friction.

Figure 5:
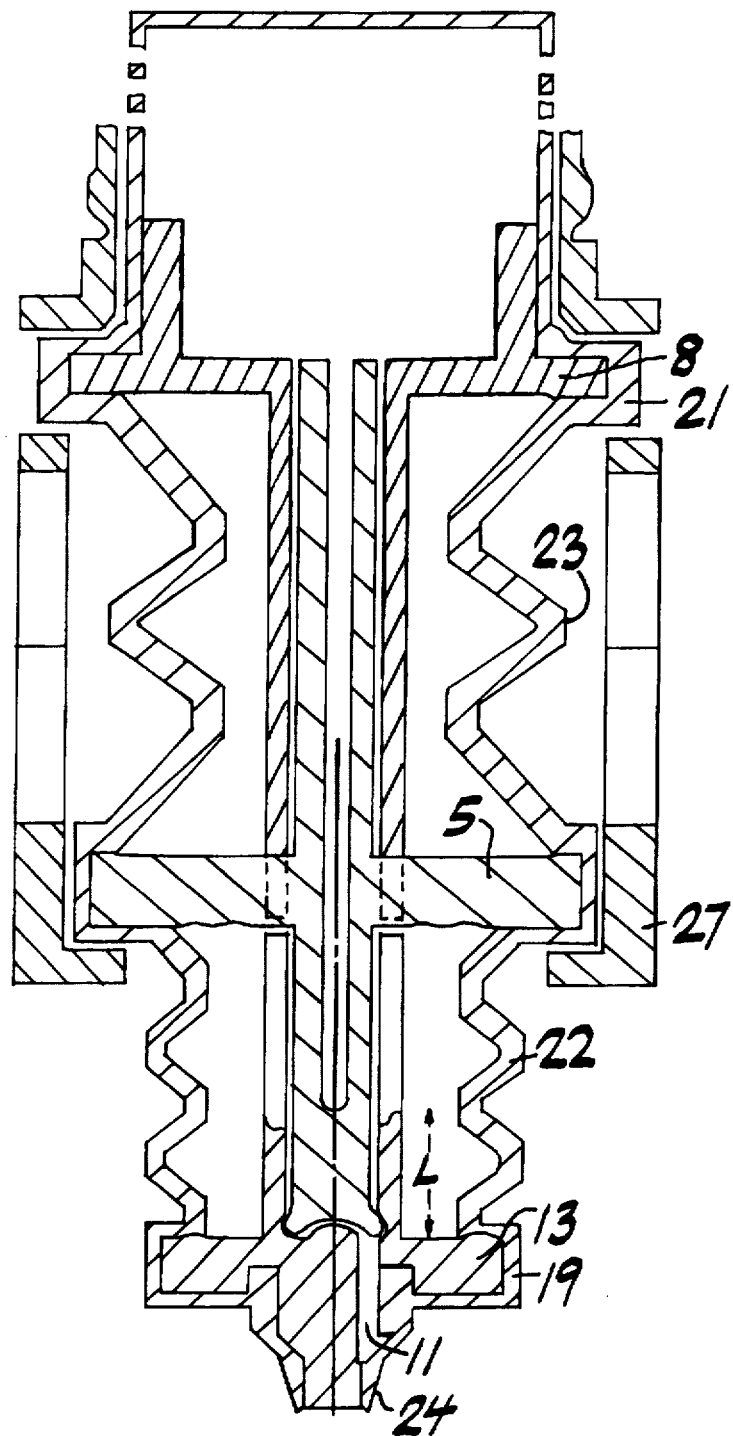
FIG. 5 is a cross-sectional view of the assembled phial-pump according to the present invention, said assembled phial-pump incorporating the piston, the pump body and the envelope shown in FIGS. 1, 2 and 4, respectively.

FIG. 5 is a schematic diagram of the assembly of three pieces similar to the above pieces, but with a few minor differences. This Figure, essentially shows the fitting of rings 13a, 5 and 8 respectively in the rings of the envelope numbered 19, 20 and 21.

Also shown are the front 22 and rear 23 concertina springs. As is clear from this Figure, length L corresponds to the backward travel of the piston inside the body enabling on the one hand the introduction of fluid into duct 18 of the pump and on the other determining, on the basis of the inside diameter of duct 18, the volume of fluid to be expelled.

FIG. 5 also shows that the pump according to the invention has been fitted inside a rigid shell 27. Also more clearly distinguishable is the annular undercut. In the cases illustrated above, in the case of projecting unitary doses of an ophthalmic liquid, the dimensions may for example be as follows:

diameter of the channel constituting the outlet orifice, and its length: approx. 0.60 mm and 3.0 mm respectively;

thickness of the Kraton envelope at the level of valve 24: approx. 0.8 mm decreasing towards the fluid outlet end;

thickness of the Kraton envelope at the level of concertina 23: 1 mm, and at concertina 22: 0.75 mm.

Lastly, we can see that the rear part of the envelope, at the top of the Figure, has been enclosed for example by sealing, so that the pump body and piston are totally enveloped with the exception of the front end of the pump body.

FIG. 6 show the dynamics of the pump. In this series of Figures, the pump has been assembled as shown in FIG. 5 inside a rigid shell. By using this rigid shell, the pump body is movable whilst the piston is held in a stationary position.

F represents the fluid with which the elastic envelope has been filled.

The dynamics of the pump are as follows:

In the at-rest position 6A, the piston is held in a stationary position by receptacle 27 of the pump, i.e. by a different structure to the three elements of the actual phial-pump. It is held secure by the compression of rear concertina spring 23.

In FIG. 6B, on activating the pump, the pump body is thrust forwards by its rear part 8 and transmits this thrust to the nose which is made integral with it by means of the sleeve. The effect of this is to create a cavity of drops in pump duct 18 in this space, which remained virtual during the pump's at-rest period and which is then of a volume determined by the height of the bottom lip of front groove 14 from sleeve 7, which places this cavity of drops 18 in communication with the cavity limited by the front concertina. This cavity of drops 18 is limited at the front by pump stop 16, at the sides by the front cylindrical part 18 of the sleeve not opened by the lateral slots 14 and, at the rear, by the front part 2 of the piston limited by front annular flange 2 of this piston.

FIG. 6C, when the nose is pushed sufficiently far forward so that front flange 2 of the piston is then behind the front lips 15 of the front grooves of sleeve 7, the depression in the cavity of drops 18 is then made up for by the arrival of fluid F. The pump is then said to be in the filled or open position.

This filled position may be locked by a ratchet system on receptacle 27 which itself will be unlocked if the user applies pressure to a pawl. The pawl forms part of the receptacle case 27 in which this pump is housed.

During activation, rear spring concertina 23 is under compression and front concertina 22 is extended.

FIG. 6D, during the stage of ejecting the drops of fluid F, i.e. when the nose and body return to their initial at-rest position, rear spring concertina 23, initially compressed, extends and the assembly resumes the at-rest position 6E.

The sealing and sterilization of the above phial can be achieved as follows:

The rear part of the piston mould is itself used for assembly purposes. This assembly is performed in a controlled filtered air environment, as soon as the piston is turned out of the hot mould, and in a controlled atmosphere. As soon as the core of the piston is withdrawn from the elastic pocket, the rear part of the elastic envelope is immediately sealed, either by heat-sealing, or by ultrasound, radio, etc. The inside of the pump is henceforth impossible to contaminate during subsequent handling. Thus, after sealing the rear part of the elastic envelope, the pump body and the piston become totally enveloped in the latter. Only the front end of the pump body becomes directly accessible from the outside of the envelope.

Just before sealing, a gas may be injected to completely sterilize the inside—a gas which will be drawn out again before injecting the formulation, this may be without preservative since the environment is perfectly sealed and sterile.

In order to minimise the cost of sterile filling systems in particular, sterilization may be performed after sealing by gamma radiation, electrons, gas, liquid, etc.

Sterilization may also be performed before heat-sealing by injecting gas or hot air during sealing.

If sterilization is performed by injecting hot air or antiseptic liquid, the pump will be placed in the activation position beforehand in order to expose to decontamination the intra-nasal channel of the pump and the front flange of the piston.

I claim:

1. A pump for the delivery of a fluid contained in an elastic phial, comprising:

a pump body having a front end on a fluid outlet side, said front end comprising an outlet orifice (11) normally sealed off by an elastic membrane (24), and continuing backwards through a pump duct (18) with a fluid inlet orifice (15);

a movable piston fitted inside the pump body, the relative displacement of an end (2) of the piston in relation to the pump body between the inlet orifice (15) and a stop (16) position located towards the outlet orifice (11) thus determining the quantity of fluid expelled on displacement, the end (2) of the piston fitting hermetically by slight friction against the pump duct (18), the inlet orifice (15) being of a sufficient size for only the preset quantity of fluid to be trapped in an end of the pump duct (18) for its expulsion through the outlet orifice (11) and a separable seam defined by interface of said outlet orifice (11) and said elastic membrane (24), the pump body and the piston being totally enveloped by the elastic phial, with the exception of the front end of the pump body.

2. The pump according to claim 1, wherein the outlet orifice (11) is a channel positioned axially along the length of the pump.

3. The pump according to claim 1, wherein the pump has an elastic means of returning the piston to the stop position.

4. The pump according to claim 3, wherein the elastic means of returning the piston to the stop position comprises the elastic phial itself.

5. The pump according to claim 4, wherein the elastic means of returning the piston to the stop position comprises a concertina part of sufficient thickness to form a means of return.

6. A pump for the delivery of a fluid contained in an elastic phial, comprising:

a pump body having a front end on a fluid outlet side, said front end comprising an outlet orifice (11) sealed off by an elastic membrane (24), and continuing backwards through a pump duct (18) with a fluid inlet orifice (15); and a movable piston fitted inside the pump body, the relative displacement of an end (2) of the piston in relation to the pump body between the inlet orifice (15) and a stop (16) position located towards the outlet orifice (11) thus determining the quantity of fluid expelled on displacement, the end (2) of the piston fitting hermetically by slight friction against the pump duct (18), the inlet orifice (15) being of a sufficient size for only the preset quantity of fluid to be trapped in an end of the pump duct (18) for its expulsion through the outlet orifice (11), the pump body and the piston being totally enveloped by the phial, with the exception of the front end of the pump body;

wherein the pump has an elastic means of returning the piston to the stop position, and wherein the elastic means of returning the piston to the stop position comprises the elastic phial itself, and wherein the elastic means of returning the piston to the stop position comprises two concertinas (22, 23) located either side of a retaining ring (5) integral with the piston.

7. The pump according to claim 5, wherein the elastic means of returning the piston to the stop position comprises two concertinas (22, 23) located either side of a retaining ring (5) integral with the piston.

8. The pump according to claim 1, wherein the elastic membrane (24) and the elastic phial form a single piece.

9. The pump according to claim 1, wherein the elastic phial has at least one part such as a thickening, adapted to filling the phial with the aid of a hollow needle, of such a type that after piercing, filling and withdrawing said hollow needle, the piercing is hermetically sealed.

10. The pump according to claim 1, wherein the pump body has a front ring (13a) and a rear ring (8).

11. The pump according to claim 1, wherein the piston has a ring (13).

12. The pump according to claim 6, wherein at least one of the ring (15), a body (8) and a disc (13a) is integral with the end of a concertina of the elastic phial.

13. A pump for the delivery of a fluid contained in an elastic phial, comprising:

a pump body having a front end on a fluid outlet side, said front end comprising an outlet orifice (11) sealed off by an elastic membrane (24), and continuing backwards through a pump duct (18) with a fluid inlet orifice (15); and a movable piston fitted inside the pump body, the relative displacement of an end (2) of the piston in relation to the pump body between the inlet orifice (15) and a stop (16) position located towards the outlet orifice (11) thus determining the quantity of fluid expelled on displacement, the end (2) of the piston fitting hermetically by slight friction against the pump duct (18), the inlet orifice (15) being of a sufficient size for only the preset quantity of fluid to be trapped in an end of the pump duct (18) for its expulsion through the outlet orifice (11), the pump body and the piston being totally enveloped by the phial, with the exception of the front end of the pump body;

wherein the piston is an elongated element having a plurality of radial elements (4) as anchors which have arc-shaped elements (5) at their ends, the pump body is cylindrical and comprises a front ring (13a), a cylindrical rear ring (8), of larger diameter than the diameter of the arcs (5), the front base of the rear cylindrical ring being cut away so that the above anchors can pass through the base of said cylinder thus enabling, by means of slots corresponding to the radial elements, and made in the cylinder comprising the pump body, the longitudinal displacement of the piston.

14. A pump, for projecting a consistently reproducible volume of fluid into the conjunctival sac of an eye essentially without causing any sensation of pain or discomfort, comprising:

a reservoir made of elastic material, a pump body in fluid communication with the reservoir, said pump body having a front end on a fluid outlet side, said front end comprising an outlet orifice (11) sealed off by an elastic membrane (24), a piston arranged to move inside the pump body and an elastic means for returning the piston to the stop position, said elastic means of return being calibrated so as to project a predetermined volume of fluid through the outlet orifice (11) and a separable seam defined by interface of said outlet orifice (11) and said elastic membrane (24); and an elastic phial enveloping the pump body and piston, with the exception of the front end of the pump body.

* * * * *

UNITED STATES PATENT AND TRADEMARK OFFICE
CERTIFICATE OF CORRECTION

PATENT NO. : 5,746,728
DATED : May 5, 1998
INVENTOR(S) : PY, Daniel

It is certified that error appears in the above-identified patent and that said Letters Patent is hereby corrected as shown below:

Column 2, line 59, change "and preferably with" to --, and preferably with,--.

Column 5, line 26, change "makes enables" to --enables--.

Column 6, line 24, change "ohpthalmology" to --ophthalmology--.

Column 8, line 6, change "4, it" to --4. It--.

Column 8, line 23, change "gel, these" to --gel: these--.

Column 8, line 39, change "position The" to --position. The--.

Column 8, line 41, change "assembly enabling the latter" to --assembly, enabling assembly--.

Column 9, line 3, change "show" to --shows--.

UNITED STATES PATENT AND TRADEMARK OFFICE
CERTIFICATE OF CORRECTION

PATENT NO. : 5,746,728
DATED : May 5, 1998
INVENTOR(S) : PY, Daniel

It is certified that error appears in the above-identified patent and that said Letters Patent is hereby corrected as shown below:

Column 9, line 60, change "formulation," to --formulation;--.

Signed and Sealed this

Twenty-second Day of December, 1998

Attest:

BRUCE LEHMAN

*Attesting Officer*   *Commissioner of Patents and Trademarks*